United States Patent [19]
Gallant

[11] 4,156,268
[45] May 22, 1979

[54] HUMIDITY SENSING ELEMENT AND METHOD OF MANUFACTURE THEREOF

[75] Inventor: Donald A. Gallant, Charlotte, N.C.

[73] Assignee: Longwood Machine Works, Inc., Woodside, N.Y.

[21] Appl. No.: 828,895

[22] Filed: Aug. 29, 1977

[51] Int. Cl.² ............................................. H01G 4/10
[52] U.S. Cl. ................................. 361/286; 29/25.42; 73/336.5; 204/38 S; 361/312; 361/322
[58] Field of Search ......................... 338/35; 73/336.5; 361/286, 322, 312; 29/25.42; 204/38 A, 38 S

[56] References Cited

U.S. PATENT DOCUMENTS

| | | | |
|---|---|---|---|
| 2,015,125 | 9/1935 | Dolin | 73/336.5 |
| 2,892,139 | 6/1959 | Salzberg | 361/312 |
| 3,458,845 | 7/1969 | Thoma | 73/336.5 X |
| 3,523,244 | 8/1970 | Goodman | 73/336.5 X |
| 3,671,913 | 6/1972 | Mamiya | 73/336.5 X |
| 3,895,271 | 7/1975 | Dudas | 361/286 |
| 3,987,676 | 10/1976 | Bennewitz | 73/336.5 |

FOREIGN PATENT DOCUMENTS

450410  8/1948  Canada .................................. 73/336.5

*Primary Examiner*—E. A. Goldberg
*Attorney, Agent, or Firm*—Richards, Shefte & Pinckney

[57] ABSTRACT

A doped capacitance humidity sensing element and method of manufacture thereof is provided. The element has a response time in the order of one second and has one electrode formed by an anodizable metal, an anodized layer thereon, conductive, metal atoms deposited in non-short-circuiting mutual relation in the interstices of the anodized layer, the anodized coating layer sealed to contact the particles with an ion-forming material and reduce the porosity of the coating, and a second electrode formed by a moisture-vapor-pervious, electron-conductive layer of metal deposited on the sealed anodized coating on the opposite side from the first electrode, the anodized coating layer being generally pervious to the surrounding gaseous atmosphere and the moisture vapor thereof and the capacitance element presenting an impedance to low frequency sine wave electrical excitation varying inversely and generally proportionally to the relative humidity of the surrounding gaseous atmosphere.

19 Claims, 3 Drawing Figures

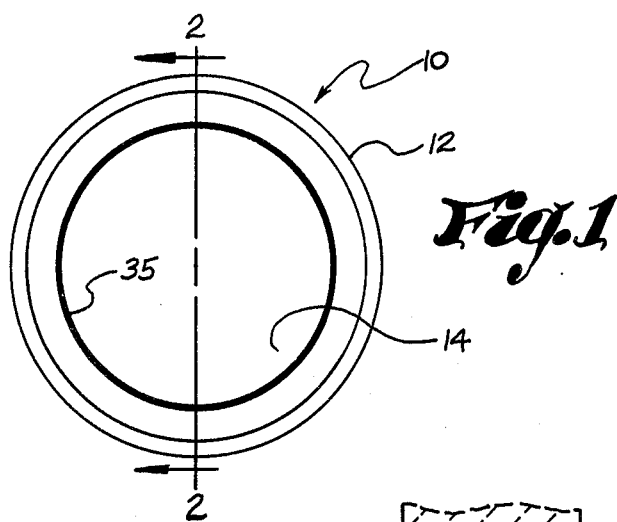
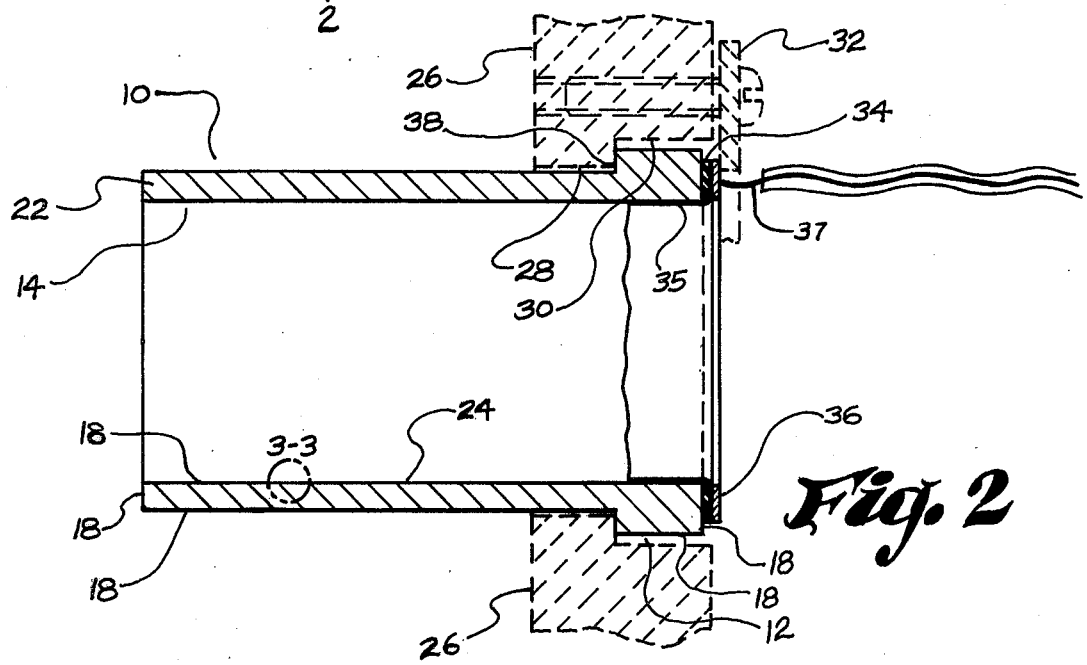
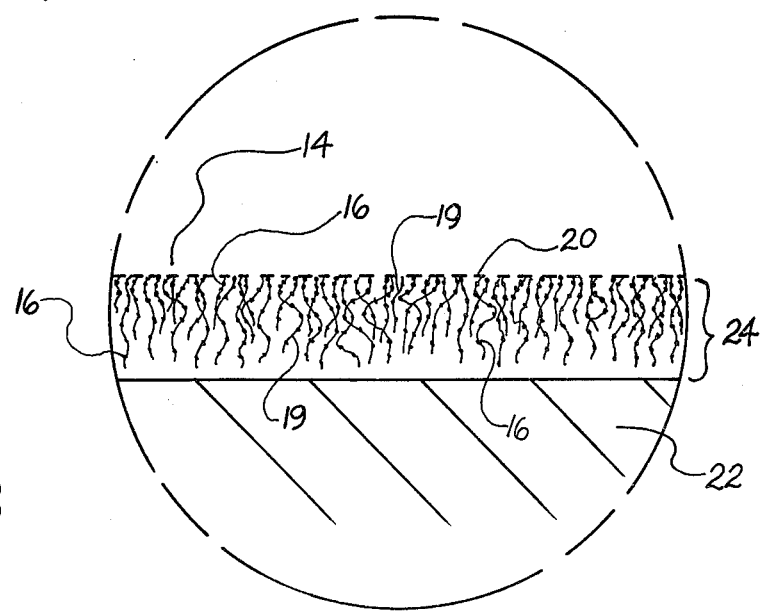

HUMIDITY SENSING ELEMENT AND METHOD OF MANUFACTURE THEREOF

BACKGROUND OF THE INVENTION

Various types of humidity sensing elements, or so-called humidity elements, have been used as the tranducers of hygrometers for quantitatively sensing the water vapor content of gaseous atmospheres. Paper, or horsehair, sensing elements which respond by relatively slow changes in length dimension to changes in atmospheric moisture content have been used for many years. More sophisticated humidity sensors such as the Dunmore cell have used layers of hygroscopic chemicals such as lithium chloride as variable resistors between the electrodes of the sensors, the electrical resistance of the lithium chloride being a function of the amount of moisture absorbed from the surrounding atmosphere and measurable by electrical instrumentation. A moisture sensing element disclosed in U.S. Pat. No. 3,748,625 has a pair of electrodes spaced apart by a crystal lattice which permits molecules of the atmosphere being monitored to randomly drift in and out of the crystal interstices due to vapor pressure changes, and the volumetric resistance of the sensor changes as a function of the percent of water vapor present in the molecules of atmosphere within the interstitial spaces.

The paper or horsehair sensing elements are slow to react to moisture changes, and their reactions must be mechanically measured with the attendant problems of stickslip friction, damage possibilities, adjustment requirements, and mechanical wear problems, and do not provide the accuracy of humidity measurement which is desired in many applications. The Dunmore cell type sensors are delicate to the extent that they can be decalibrated by a fingerprint, and in that their hygroscopic nature gathers moisture from the atmosphere which may create a high humidity zone around the sensor with resultant inaccuracies in measurements. The sensor of U.S. Pat. No. 3,748,625 requires long and involved processes and results in a sensor which would appear to require special housing for physical protection.

In contrast, the present invention provides a relative humidity sensing element that may be energized or excited by low voltage microscopic currents from solid state electronic instrumentation, does not depend on mechanical movements, is physically sturdy and requires no special physical protection, is not affected by fingerprints or reasonably dirty environments, is non-hygroscopic so that moisture only permeates the element and is not attracted by it nor collected in it, has a response time on the order of one second, and is manufactured by a method comprised by a novel combination of familiar and non-exotic manufacturing methods.

SUMMARY OF THE INVENTION

The humidity sensing element for gaseous fluids of the present invention comprises a first electron conductive electrode, a porous coating of dielectric thereon, minute particles of electron conductive material deposited in the interstices of the porosity of the dielectric, a second electron conductive electrode pervious to moisture vapor and disposed on the dielectric coating on the opposite side thereof from the first electrode, an ion-forming material in the dielectric commonly contacting the particles and the second electrode and reducing the porosity of the dielectric, the impedance between the electrodes varying generally linearly with relation to the relative humidity of the surrounding gaseous atmosphere in a suitable range of interest when excited by a suitable alternating current voltage.

Briefly described, the humidity element of the present invention has the first electrode formed from commercially pure anodizable metal, an anodized layer thereof forms the dielectric coating, the minute particles deposited therein are metal and the ion-forming material contacting them reduces the porosity of the dielectric, the impedance between the electrodes is a capacitance-resistance combination, and the second electrode is formed by vacuum deposition of metal from a plated hot filament onto the anodized layer.

Preferably the humidity sensing element of the present invention has had the dielectric beneath the second electrode formed by oxalic acid anodizing on a portion of the sensing element having an initial surface finish roughness of about 8 micro inches root means square, minute particles of nickel have been deposited in the porosity of the dielectric, the anodized dielectric has been hydrolized and sealed to contact the nickel particles with ion-forming material, and the second electrode is formed by a deposit of nickel in quantity equivalent to an amount calculated for deposition of a layer approximately 100 Angstrom units thick on a smooth non-porous surface.

In the preferred embodiment, the humidity element of this invention has the first electrode formed from 99.4% pure aluminum which is anodized to a thickness in the range of about 0.02 to 0.08 millimeters, atom-sized nickel particles are deposited in the interstices of the anodized dielectric while it is dry and unsealed by vacuum deposition from a hot nickel-plated filament in a quantity equivalent to an amount calculated to deposit on a smooth non-porous surface a layer between 5 and 10 Angstrom units thick, and the element is suitable for excitating for sensing by an alternating current sine wave voltage in the order of 10 Hertz for optimizing the temperature effects on the linearity of the decreasing impedance with increasing relative humidity relationship of the element. It is preferred to make electrical contact with the second electrode by a coating of electrically conductive material covering a portion of the second electrode and also covering an otherwise exposed portion of an insulating and cushioning element adhered to the sensing element so that a pressure contact electrical connection to the conductive material and thereby to the second electrode may be made by pressure on the cushioning element without shorting the second electrode to the first electrode by inadvertently crushing the dielectric between them.

Briefly described, the method of manufacturing the humidity sensing element of the present invention comprises the steps of coating at least a portion of a first electron conductive electrode with a porous coating of dielectric, depositing minute particles of electron conductive material in the interstices of the porosity of the dielectric, commonly contacting the particles in the interstices by means of an ion-forming material, and forming a second electron conductive electrode contacting the ion-forming material and pervious to moisture vapor and disposed on the dielectric coating on the opposite side thereof from the first electrode whereby the impedance between the electrodes varies generally linearly with relation to the relative humidity of the surrounding gaseous atmosphere in a suitable range of interest when excited by a suitable alternating current voltage.

Preferably, the method of manufacturing for the present humidity element includes forming the first electrode from commercially pure aluminum and anodizing the aluminum to form the dielectric coating, vacuum depositing atomic particles of nickel from a hot filament into the interstices of the porosity of the dielectric in a quantity equivalent to an amount calculated to deposit a layer of thickness between 5 and 10 Angstrom units on a smooth non-porous surface, contacting the particles in the interstices by hydrolizing and sealing the anodized coating, and vacuum depositing nickel onto the sealed anodized coating to form the second electrode.

The preferred method of manufacturing the present humidity element includes oxalic acid anodizing the aluminum to a thickness of about 0.02 to 0.08 millimeters, and depositing nickel for the second electrode in a quantity equivalent to an amount calculated to deposit a layer about 100 Angstrom units thick on a smooth non-porous surface.

BRIEF DESCRIPTION OF THE DRAWINGS

FIG. 1 is an axial view of a typical cylindrical sensing element according to the present invention;

FIG. 2 is a longitudinal cross sectional view taken along the line 2—2 of FIG. 1 and showing in phantom typical mounting and electrical connection arrangements for the sensing element; and FIG. 3 is an enlarged schematic cross sectional view taken generally within the circular area designated 3—3 in FIG. 2.

DESCRIPTION OF THE PREFERRED EMBODIMENT

The humidity element, or humidity sensing element, of the preferred embodiment of the present invention is suitable for excitation by a ten Hertz sine wave alternating current electrical voltage impressed across its electrodes by a solid state electronic measurement circuit and consists essentially of a tubular aluminum first electrode member whose bore has been anodized, the anodized layer impregnated in its porosity with nickel particles by vacuum deposition, the anodized layer sealed, and the sealed anodized layer overlaid with a porous vacuum deposition of nickel to form a second electrode.

The sensing element 10 as shown in FIGS. 1 and 2 is typically a small, hollow cylinder of commercially pure (99.4%) aluminum, such as Alloy 1100, having an outer flange 12 for mounting purposes at one end. The hollow bore 14 of the sensing element 10 is typically machined to a very fine finish and then roller burnished to a very smooth, about 8 micro inch, surface finish. A typical element 10 has a bore of about 15 millimeter diameter, 32 millimeter length, and a wall thickness of about 15 millimeters.

The entire element 10 is initially anodized by conventional methods in a 3 percent solution by weight of oxalic acid in distilled water at ambient temperature at a current density of 12 amperes per square foot for 60 to 70 minutes to achieve an anodized coating or layer of aluminum oxide or alumina ($Al_2O_3$) of about 0.02 to 0.08 millimeters thickness. This anodized layer is then thoroughly rinsed to remove the acid and is then dried at about 38 degrees C. for 24 hours.

The anodized layer has an open pore structure probably similar to a miniaturized layer of rocks, probably formed by amorphous agglomerations of aluminum oxide molecules which grow bouldered-up from the essentially pure aluminum base metal during the anodizing process, and it is nearly impervious at the metal base and ever more porous toward the surface of the layer. In the preferred embodiment disclosed here, the hollow bore 14 of the sensing element 10 forms the moisture sensing portion of the element, and it is therefore suitably treated to deposit minute particles 16 of a suitable metal such as nickel into the interstices 19 (as schematically represented in FIG. 3) of the porosity of the anodized layer 18 inside the bore 14.

In the preferred method of manufacture of the present sensor, the anodized layer 18 within the hollow bore 14, having been rinsed and dried, is exposed to vacuum deposition bombardment by atoms of nickel by heating a solid tungsten wire centered axially within the bore 14, the tungsten wire having been previously electroplated with a quantity of nickel equivalent to an amount calculated at 95% plating efficiency to be sufficient to form a layer of nickel 5 to 10 Angstrom units thick at 95% deposition efficiency if the surface of the bore 14 were smooth and solid. However, since the surface of the bore 14 is microscopically highly porous, the atoms of nickel will be randomly deposited within the interstices of the porosity of the anodized layer 18, in decreasing quantities down into the layer 18 toward the base metal, and the atoms of nickel will adhere to the interstitial surfaces of the anodized layer 18 as is typical of vacuum deposition. The preferred method of vacuum deposition is at a calculated tungsten wire temperature of 2600° F. for 15 seconds in a $10^{-5}$ to $10^{-6}$ torr vacuum.

Following deposition of the nickel particles 16 on the unsealed anodized layer 18, the sensing element or sensor 10 is placed in a boiling water bath to hydrolize and seal the anodized layer 18 as is common in anodizing practice. Thereafter, the sensor 10 should be thoroughly dried at about 150° F. before the next step. Sealing partially converts the as-anodized alumina of the anodized layer 18 to an aluminum monohydrate, and this reduces the porosity of the anodized layer 18 somewhat, as well as leaving the nickel particles 16 in contact with the ion-forming aluminum monohydrate probably containing residual traces of oxalic acid and layer 18 vapor pervious.

It is next desirable to form a thin, water vapor pervious electrode over the nickel-impregnated sealed anodized layer 18 which lies within the bore 14, and this is again preferably accomplished by vacuum deposition of nickel atoms on the surface of the bore from a nickel-plated axially centered tungsten wire for 15 seconds at a temperature of 2600° F. in a $10^{-5}$ to $10^{-6}$ torr vacuum. The amount of nickel in this deposition is calculated at 95% plating efficiency to be equivalent to that amount which would form a layer 100 Angstrom units thick at 95% deposition efficiency if the surface of the bore 14 were smooth and solid. However, due to the porosity of the sealed anodized layer 18 and the thinness of the nickel deposition, a probably lacy deposit of nickel is formed which is pervious to atmospheric molecules while being electrically conductive to form a second electrode 20 separated from the first electrode formed by the aluminum body 22 of the sensor 10 by the doped dielectric layer 24 formed by the nickel impregnated sealed portion of the anodized layer 18.

As shown in FIGS. 1 and 2, the sensor 10 may be suitably mounted in a mounting bracket 25 suitably provided with a bore 28 and a counterbore 30 for receiving the cylindrical portion and the flange 12 of the sensor 10, and a clamping ring 32 of non-conductive or insulating material equipped with suitable screws for engagement with threaded holes in the bracket 26 for firmly mounting the sensor 10. To facilitate a suitable pressure electrical contact with the second electrode 20 without inadvertent crushing of the doped dielectric layer 24 that could effectively short circuit the two electrodes, a thin plastic insulating ring 34 is adhesively fastened to the flanged outer end of the sensor 10, the ring 34 having the same inside diameter as the sensor 10 and an outside diameter slightly less than that of the flange 12, and a layer 35 of electrically conductive material, such as conductive paint or metallic ink, is applied as shown in FIG. 2 to cover the second electrode 20 for a short distance within the bore 14 and to extend unbroken over the inside diameter of the plastic ring 34 and over its exposed flat surface. A suitable metal ring 36 of approximately the same diameter dimensions as the ring 34 and having an electrical conductor 37 connected thereto, may then be clamped over the conductive layer 35 by the insulating clamping ring 32. Electrical connection to the first electrode formed by the aluminum body 22 is suitably made by machining the anodized layer 18 from the underside 38 of the flange 12 for pressure contact with the mounting bracket 26 which is suitably at ground potential for eliminating stray current effects on the sensor 10. Thus, the sensor 10 is self-contained and forms its own protection for the humidity-sensitive portion in its bore, while the surrounding atmosphere may circulate freely through the bore (which is normally mounted vertically) for free exchange of atmospheric molecules with the dielectric layer 24.

The exact means by which the sensor of this invention functions to have an impedance which decreases generally linearly proportionally to the relative humidity of the atmosphere to which it is exposed must be a subject for theorizing. However, the invention of the present sensor was based on the theory that while the capacitance of a porous dielectric between electrodes will increase linearly with the number of water vapor molecules present in the dielectric, the resistance of many materials increases as the temperature increases, so that in theory, a suitable combination of capacitance and resistance in a humidity sensing element should result in a humidity element which responds essentially linearly proportionally to the relative humidity of the atmosphere to which it is exposed. This may be explained by the facts that relative humidity is essentially defined as the ratio of the specific quantity of water vapor in a given volume of air at a given temperature, compared to the maximum specific quantity of water vapor which the same volume of air could hold in vapor form at that temperature, and that a rise in the temperature of air containing a specific quantitiy of moisture vapor causes the relative humidity to go down, and vice versa, and that an increase in the specific amount of moisture vapor in a volume of air held at constant temperature causes the relative humidity to rise, and vice versa. Thus, in theory, the ideal humidity sensing element should combine capacitance and electrical resistance in a suitable manner such that its total impedance will vary essentially linearly proportionally with the relative humidity; that is, when the temperature rises while the moisture vapor molecules in the atmosphere remain constant, the resistance should rise, while the capacitance remains constant, resulting in an increasing total impedance with rising temperature, and vice versa. Also, when the atmospheric temperature remains constant, and the number of water vapor molecules therein is increased, then the capacitance of the sensor should increase, and its impedance thereby decrease, while its resistivity remains constant and its total impedance thereby decreases, and vice versa. Such a combination results in a sensor whose impedance varies inversely proportionally to the relative humidity of the atmosphere, and when such a sensor is connected in series with a resistance and excited by a suitable alternating current voltage, the voltage drop across the series resistor will vary directly as the relative humidity of the atmosphere.

In theory, again, water vapor molecules within the dielectric of a capacitance become polarized, but are non-conductive and only serve to increase the capacitance of the dielectric. In the present sensing element, water vapor molecules in the presence of the ion-forming aluminum monohydrate in contact with the nickel particles in the anodized layer 18 will form conductive ionization paths between the nickel particles and lower the resistance in the path between the electrodes, yet and resistance paths are affected by temperature increases to increase their resistance. The end result of the preferred embodiment disclosed herein is that the combination of resistance, which is responsive both to water molecules and to temperature changes, combined with the capacitance, which is essentially responsive to the presence of water vapor molecules, forms a sensor whose impedance is essentially linearly inversely proportional to the relative humidity of the atmosphere to which it is exposed, and the impedance changes almost instantly in response to relative humidity changes (response time in the order of 1 second) due to the thin and molecularly porous dielectric and second electrode.

While it has not been determined what specific conditions would give a perfectly linear relation between sensor impedance and relative humidity, it has been determined that the relation is sufficiently linear in the present sensor for effective performance in a suitable range of temperatures and humidities as normally must be controlled in typical textile mills, which may typically require temperatures between 75° F. and 85° F. and relative humidities between 40% and 85%. It has been found that the present sensor varies notably from a linear response when excited by 60 Hertz AC voltage, but that linearity is improved when it is excited with 20 Hertz AC voltage, and that it is improved still further when excited by 10 Hertz AC voltage, to the extent that 10 Hertz excitation provides substantial linearity for the commercial humidity controls for which the present sensor is designed.

Among other limiting conditions to the present sensor, it has been found that excessive impurities in the aluminum will result in an anodized layer 18 containing unanodized alloying particles which will effectively short circuit between the two electrodes, but the commercially available electrical conductor Alloy 1100 functions suitably. Likewise, if the calculated thickness of nickel deposited in the porosity of the anodized layer 18 exceeds 10 Angstrom units, the two electrodes again tend to become shorted out, while a calculated thickness of less than 5 Angstrom units fails to supply the resistive component of impedance between the two electrodes which is desired. Also, the anodized layer 18 achieved in the bore 14 after it has been fine machined and roller burnished to a surface finish approximating 8 micro inches by an anodizing bath consisting of a 3% solution by weight of oxalic acid in distilled water at room temperature for 60 to 70 minutes at a current density reaching 12 amperes per square foot has been found satisfactory, and is believed to lie in the range of 0.02 to 0.08 millimeters thickness. Hydrolizing and sealing the anodized layer 18 decreases the porosity of the anodized layer such that the deposited second electrode 20 on the anodized layer 18 does not get down into the porosity of the anodization enought to short out the nickel atoms already deposited therein. It has been found that sulfuric acid or nitric acid anodized layers, when sealed, apparently contain so much residual ion-forming material that they effectively short circuit the two electrodes and are therefore unsatisfactory, and oxalic acid, which is an organic acid, has been found to give suitable results. Similarly, when the second electrode 20 was deposited with a calculated thickness of 25 Angstrom units, it was found to be non-conductive, 50 Angstrom units was conductive, but 100 Angstrom units appears to be best for conductance and porosity, while 200 Angstrom units is not sufficiently porous and permeable.

It is recognized that there may be variables in the dimensions, materials, and processes for manufacturing humidity elements according to the concepts of the present invention, and this preferred embodiment presents a workable element and method of manufacture therefor, which is disclosed in full detail and illustrated in the drawings for disclosure purposes only, but it is not intended to limit the scope of the present invention, which is to be determined by the scope of the appended claims.

I claim:

1. A humidity sensing element for gaseous fluids comprising a first electron conductive electrode, a porous coating of dielectric suitable for hydrolization formed on and from said first electrode, atoms of electron conductive material randomly deposited and adhered in generally non-short-circuiting mutual relation in the interstices of the porosity of said dielectric as formed, ion-forming material formed from at least partial conversion of said coating to said ion-forming material by hydrolization of said coating, said dielectric being in a hydrolized state and a second electron conductive electrode pervious to moisture vapor and disposed on said hydrolized dielectric coating on the opposite side thereof from said first electrode, said ion-forming material commonly contacting said dielectric, said atoms, and said second electrode.

2. A humidity element for gaseous fluids according to claim 1 and characterized further in that said first electrode is formed from commercially pure anodizable metal.

3. A humidity element for gaseous fluids according to claim 2 and characterized further in that said anodizable metal is aluminum.

4. A humidity element for gaseous fluids according to claim 3 and characterized further in that said first electrode had an initial surface finish roughness approximating 8 micro inches root mean square in the area to be beneath said second electrode.

5. A humidity element for gaseous fluids according to claim 1 in which said first electrode is formed from commercially pure anodizable metal and characterized further in that said coating of dielectric comprises an anodized layer.

6. A humidity element for gaseous fluids according to claim 5 and characterized further in that said anodized layer is oxalic acid anodized.

7. A humidity element for gaseous fluids according to claim 6 and characterized further in that said anodized layer has a thickness in the approximate range of 0.02 to 0.08 millimeters.

8. A humidity element for gaseous fluids according to claim 1 and characterized further in that said first electrode is formed from commercially pure anodizable metal, said coating is an anodized layer, and said atoms are composed of nickel.

9. A humidity element for gaseous fluids according to claim 8 and characterized further in that the quantity of said atoms is equivalent to an amount calculated to deposit on a smooth non-porous surface a layer of thickness between 5 and 10 Angstrom units.

10. A humidity element for gaseous fluids according to claim 1 and characterized further in that said first electrode is formed from commercially pure anodizable metal, said coating is an anodized layer, and said atoms are metal.

11. A humidity element for gaseous fluids according to claim 1 and characterized further in that said first electrode is formed from commercially pure anodizable metal, said dielectric is formed by an anodized layer, said atoms are metal, and the impedance between said electrodes comprises a capacitance-resistance combination.

12. A humidity element for gaseous fluids according to claim 11 and characterized further by suitability for excitation for sensing by an alternating current sine wave voltage in the order of ten Hertz, for providing substantial linearity of the relation of said impedance to the relative humidity of said gaseous fluids.

13. A humidity element for gaseous fluids according to claim 1 and characterized further in that said first electrode is formed from commercially pure anodizable metal, said dielectric is formed by an anodized layer, said atoms are nickel, and said second electrode comprises metal disposed by vacuum deposition from a plate hot filament.

14. A humidity element for gaseous fluids according to claim 13 and characterized further in that said second electrode metal deposit is composed of a quantity of nickel equivalent to an amount calculated to deposit a layer of thickness approximating 100 Angstrom units on a smooth non-porous surface.

15. A humidity element for gaseous fluids according to claim 13 and characterized further by an insulating and cushioning element adhered to said sensing element, a coating of electrically conductive material covering a portion of said second electrode and covering a portion of said insulating and cushioning element not adhered to said second electrode to provide for pressure contact electrical connection to said conductive coating material and thereby to said second electrode without shorting said second electrode to said first electrode upon inadvertent crushing of said dielectric between said electrodes.

16. A humidity sensing element for gaseous fluids in the form of a doped capacitance-resistance member comprising a first electrode of commercially pure anodizable metal, a porous dielectric layer of an oxalic acid anodized coating formed on said electrode, atoms of metal randomly deposited and adhered in generally non-short-circuiting mutual relation within the interstices of said anodized coating as formed, said anodized coating hydrolized and sealed to contact said atoms with ion-forming material while retaining but decreasing the porosity of said coating, and a second electrode formed by a moisture-vapor-pervious electron-conductive deposit of metal on said sealed anodized coating on the opposite side thereof from said first electrode, said capacitance-resistance member having an impedance between said electrodes varying inversely and generally proportionally to the relative humidity of the surrounding gaseous atmosphere in a suitable range of interest when excited by a suitable alternating current voltage.

17. A method of manufacturing a humidity sensing element for gaseous fluids comprising the steps of coating at least a portion of a first electron-conductive electrode with a porous coating of hydrolizable dielectric formed therefrom, depositing and adhering atoms of electron-conductive material randomly in generally non-short-circuiting mutual relation in the interstices of the porosity of said dielectric as formed, commonly contacting said dielectric and said atoms in said interstices with ion-forming material by at least partial conversion of said dielectric thereto by hydrolization thereof, and forming a second electron-conductive electrode contacting said ion-forming material and being pervious to moisture vapor and disposed on said hydrolized dielectric coating on the opposite side thereof from said first electrode.

18. A method of manufacturing a humidity element for gaseous fluids according to claim 17 and characterized further in that said first electrode is of commercially pure aluminum and said step of coating comprises anodizing said aluminum to form said dielectric coating thereon, said step of depositing comprises vacuum deposition of atoms of nickel from a hot filament into said interstices in a quantity equivalent to an amount calculated to deposit a layer of thickness between 5 and 10 Angstrom units on a smooth non-porous surface, and said step of forming said second electrode comprises vacuum depositing nickel onto said hydrolized dielectric coating to form said second electrode.

19. A method of manufacturing a humidity element for gasous fluids according to claim 18 and characterized further in that said anodizing comprises oxalic acid anodizing said aluminum to a thickness of about 0.02 to 0.08 millimeters, and said second electrode depositing comprises depositing nickel in a quantity equivalent to an amount calculated to deposit a layer of thickness of about 100 Angstrom units on a smooth non-porous surface.

* * * * *

UNITED STATES PATENT OFFICE
CERTIFICATE OF CORRECTION

Patent No. 4,156,268      Dated May 22, 1979

Inventor(s) Donald A. Gallant

It is certified that error appears in the above-identified patent and that said Letters Patent are hereby corrected as shown below:

Column 2, line 37, delete "excitating" and insert therefor --excitation--. Column 2, line 47, after "conductive" insert --coating--. Column 6, line 22, delete "and" and insert therefor --the--. Column 7, line 8, delete "enought" and insert therefor --enough--. Column 8, line 38, delete "plate" and insert therefor --plated--. Column 10, line 17, delete "gasous" and insert therefor --gaseous--.

Signed and Sealed this

Sixth Day of May 1980

[SEAL]

Attest:

SIDNEY A. DIAMOND

Attesting Officer    Commissioner of Patents and Trademarks